(12) United States Patent
Steinberg

(10) Patent No.: US 7,255,712 B1
(45) Date of Patent: Aug. 14, 2007

(54) BONE GROWTH PROMOTING IMPLANT

(75) Inventor: Amiram Steinberg, Avihail (IL)

(73) Assignee: Active Implants Corporation, Memphis, TN (US)

( * ) Notice: Subject to any disclaimer, the term of this patent is extended or adjusted under 35 U.S.C. 154(b) by 0 days.

(21) Appl. No.: 08/842,680

(22) Filed: Apr. 15, 1997

(51) Int. Cl.
*A61F 2/28* (2006.01)
*A61B 17/58* (2006.01)

(52) U.S. Cl. ............... 623/16.11; 606/63; 623/23.47

(58) Field of Classification Search .......... 606/60, 606/63, 70, 74, 105; 623/16.11, 23.31, 23.32, 623/23.47, 23.5
See application file for complete search history.

(56) References Cited

U.S. PATENT DOCUMENTS

| | | | |
|---|---|---|---|
| 2,765,787 A | 10/1956 | Pellet | |
| 3,576,133 A | 4/1971 | Walter et al. | |
| 3,600,718 A | 8/1971 | Boone | |
| 3,759,257 A * | 9/1973 | Fischer et al. | 606/63 |
| 3,846,846 A * | 11/1974 | Fischer | 623/23.18 |
| 3,875,594 A | 4/1975 | Swanson | |
| 3,879,767 A | 4/1975 | Substand | |
| 3,938,198 A | 2/1976 | Kahn et al. | |
| 4,089,071 A | 5/1978 | Kalnberz et al. | |
| 4,227,518 A * | 10/1980 | Aginsky | 606/63 |
| 4,231,120 A * | 11/1980 | Day | 623/23.24 |
| 4,245,359 A * | 1/1981 | Stuhmer | 606/95 |
| 4,279,041 A | 7/1981 | Bucholz | |
| 4,292,695 A | 10/1981 | Koeneman | |
| 4,344,193 A | 8/1982 | Kenny | |
| 4,433,440 A | 2/1984 | Cohen | |
| 4,447,915 A * | 5/1984 | Weber | 606/95 |
| 4,570,270 A | 2/1986 | Oechsle, III | |
| 4,624,674 A | 11/1986 | Pappas et al. | |
| 4,650,491 A | 3/1987 | Parchinski | |
| 4,661,112 A | 4/1987 | Muller | |
| 4,662,889 A | 5/1987 | Zichner et al. | |
| 4,664,668 A | 5/1987 | Beck et al. | |
| 4,715,859 A | 12/1987 | Schelhas et al. | |
| 4,735,625 A | 4/1988 | Davidson | |
| 4,795,470 A | 1/1989 | Goymann et al. | |
| 4,795,474 A | 1/1989 | Horvath | |
| 4,808,186 A | 2/1989 | Smith | |
| 4,813,962 A | 3/1989 | Deckner et al. | |
| 4,822,365 A | 4/1989 | Walker et al. | |
| 4,828,563 A * | 5/1989 | Muller-Lierheim | 623/23.63 |

(Continued)

FOREIGN PATENT DOCUMENTS

DE    2247721    4/1974

(Continued)

*Primary Examiner*—David J. Isabella
(74) *Attorney, Agent, or Firm*—Kelley Drye & Warren LLP (57) ABSTRACT

A stem-like bone implant includes longitudinal structural members and tension cables that provide curvature control and support, and rigidity against bending and buckling. The longitudinal structural members and tension cables may become an integral part of a composite regenerated bone having a substantially increased strength over natural bone. The flexibility of the implant is controlled by specifically varying the structural geometry of certain portions of the implant, and by adjusting the tension in the tension cables before, during and after the implantation operation to thereby adjust the stiffness of the implant. The tension cables may be adjusted to produce asymmetric or non-uniform levels of tension in the longitudinal structural members.

13 Claims, 7 Drawing Sheets

U.S. PATENT DOCUMENTS

| | | |
|---|---|---|
| 4,888,020 A | 12/1989 | Horber |
| 4,892,551 A | 1/1990 | Haber |
| 4,904,269 A | 2/1990 | Elloy et al. |
| 4,908,035 A | 3/1990 | Deckner et al. |
| 4,919,674 A | 4/1990 | Schelhas |
| 4,919,678 A | 4/1990 | Kranz |
| 4,936,856 A | 6/1990 | Keller |
| 4,938,771 A | 7/1990 | Vecsei et al. |
| 4,938,773 A | 7/1990 | Strand |
| 4,950,298 A | 8/1990 | Gustilo et al. |
| 4,955,912 A | 9/1990 | Berchem |
| 4,955,919 A | 9/1990 | Pappas et al. |
| 4,963,153 A | 10/1990 | Noesberger et al. |
| 4,963,154 A | 10/1990 | Anapliotis et al. |
| 4,997,444 A | 3/1991 | Farling |
| 4,997,447 A | 3/1991 | Shelley |
| 5,002,579 A | 3/1991 | Copf et al. |
| 5,002,581 A | 3/1991 | Paxson et al. |
| 5,011,497 A | 4/1991 | Persson et al. |
| 5,019,107 A | 5/1991 | Schelhas |
| 5,032,134 A | 7/1991 | Lindwer |
| 5,041,140 A | 8/1991 | Teinturier |
| 5,049,393 A | 9/1991 | Noon et al. |
| 5,080,675 A | 1/1992 | Lawes et al. |
| 5,080,677 A | 1/1992 | Shelley |
| 5,080,678 A | 1/1992 | Sportorno et al. |
| 5,108,446 A | 4/1992 | Wagner et al. |
| 5,108,449 A | 4/1992 | Gray |
| 5,108,451 A | 4/1992 | Forte |
| 5,116,374 A | 5/1992 | Stone |
| 5,133,762 A | 7/1992 | Branemark |
| 5,133,763 A | 7/1992 | Mullers |
| 5,146,933 A | 9/1992 | Boyd |
| 5,147,406 A | 9/1992 | Houston et al. |
| 5,151,521 A | 9/1992 | Morita et al. |
| 5,156,631 A | 10/1992 | Meriette |
| 5,171,276 A | 12/1992 | Casparia et al. |
| 5,181,925 A | 1/1993 | Houston |
| 5,181,929 A | 1/1993 | Prats et al. |
| 5,181,930 A * | 1/1993 | Dumbleton et al. ...... 623/23.34 |
| 5,197,987 A | 3/1993 | Koch et al. |
| 5,197,989 A | 3/1993 | Hinckfuss et al. |
| 5,201,881 A | 4/1993 | Evans |
| 5,201,882 A | 4/1993 | Paxson |
| 5,211,666 A | 5/1993 | Feto |
| 5,217,498 A | 6/1993 | Henssge et al. |
| 5,217,499 A | 6/1993 | Shelley |
| 5,222,985 A | 6/1993 | Homsy |
| 5,246,461 A | 9/1993 | Tepic |
| 5,281,226 A | 1/1994 | Davydov et al. |
| 5,282,868 A | 2/1994 | Bahler |
| 5,290,314 A | 3/1994 | Koch et al. |
| 5,314,478 A | 5/1994 | Oka et al. |
| 5,314,492 A | 5/1994 | Hamilton et al. |
| 5,314,493 A | 5/1994 | Mikhail |
| 5,314,494 A | 5/1994 | Huiskes et al. |
| 5,316,550 A | 5/1994 | Forte |
| 5,323,765 A | 6/1994 | Brown |
| 5,326,376 A | 7/1994 | Warner et al. |
| 5,330,534 A | 7/1994 | Herrington et al. |
| 5,336,268 A | 8/1994 | Rispeter |
| 5,344,459 A | 9/1994 | Swartz |
| 5,358,525 A | 10/1994 | Fox et al. |
| 5,364,839 A | 11/1994 | Gerhart et al. |
| 5,370,699 A | 12/1994 | Hood et al. |
| 5,373,621 A | 12/1994 | Ducheyne et al. |
| 5,376,064 A | 12/1994 | Cerny |
| 5,376,120 A | 12/1994 | Sarver et al. |
| 5,376,123 A | 12/1994 | Klaue et al. |
| 5,376,125 A | 12/1994 | Winkler |
| 5,376,126 A | 12/1994 | Lin |
| 5,387,244 A | 2/1995 | Breard |
| 5,389,107 A | 2/1995 | Nassar et al. |
| 5,393,739 A | 2/1995 | Bentz et al. |
| 5,397,359 A | 3/1995 | Mittelmeier et al. |
| 5,405,394 A | 4/1995 | Davidson |
| 5,405,403 A | 4/1995 | Mikhail |
| 5,405,411 A | 4/1995 | McCoy |
| 5,413,610 A | 5/1995 | Amino et al. |
| 5,415,662 A | 5/1995 | Ferrante et al. |
| 5,425,779 A | 6/1995 | Schlosser et al. |
| 5,433,750 A | 7/1995 | Gradinger et al. |
| 5,443,483 A | 8/1995 | Kirsch |
| 5,443,512 A | 8/1995 | Parr et al. |
| 5,448,489 A | 9/1995 | Reuben |
| 5,458,643 A | 10/1995 | Oka et al. |
| 5,458,651 A | 10/1995 | Lawes |
| 5,480,437 A | 1/1996 | Draenert |
| 5,480,449 A | 1/1996 | Hamilton et al. |
| 5,489,311 A | 2/1996 | Cipolletti |
| 5,491,882 A | 2/1996 | Walston et al. |
| 5,496,375 A | 3/1996 | Sisk et al. |
| 5,507,814 A | 4/1996 | Gilbert et al. |
| 5,507,817 A | 4/1996 | Craig et al. |
| 5,507,818 A | 4/1996 | McLaughlin |
| 5,507,820 A | 4/1996 | Pappas |
| 5,507,823 A | 4/1996 | Walston et al. |
| 5,507,829 A | 4/1996 | Thongpreda et al. |
| 5,507,830 A | 4/1996 | DeMane et al. |
| 5,507,832 A | 4/1996 | Michielli et al. |
| 5,507,833 A | 4/1996 | Bohn |
| 5,507,834 A | 4/1996 | Laghi |
| 5,507,835 A | 4/1996 | Jore |
| 5,507,836 A | 4/1996 | Pohlig |
| 5,510,418 A | 4/1996 | Rhee et al. |
| 5,514,182 A | 5/1996 | Shea |
| 5,514,184 A | 5/1996 | Doi et al. |
| 5,522,894 A | 6/1996 | Draenert |
| 5,522,904 A | 6/1996 | Moran et al. |
| 5,641,323 A | 6/1997 | Caldarise |
| 5,658,345 A | 8/1997 | Willi |
| 5,660,225 A | 8/1997 | Saffran |
| 5,743,918 A | 4/1998 | Calandruccio et al. |
| 5,755,799 A | 5/1998 | Oehy et al. |
| 5,755,801 A | 5/1998 | Walker et al. |
| 5,755,804 A | 5/1998 | Schmotzer et al. |
| 5,755,810 A | 5/1998 | Cunningham |
| 5,755,811 A | 5/1998 | Tanamal et al. |
| 5,766,257 A | 6/1998 | Goodman et al. |
| 5,766,260 A | 6/1998 | Whiteside |
| 5,776,202 A | 7/1998 | Copf et al. |
| 5,782,925 A | 7/1998 | Collazo et al. |
| 5,782,928 A | 7/1998 | Ries et al. |
| 5,788,704 A | 8/1998 | Timperley |
| 5,800,553 A | 9/1998 | Albrektsson et al. |
| 5,800,554 A | 9/1998 | Scholz |
| 5,800,555 A | 9/1998 | Gray, III |
| 5,800,557 A | 9/1998 | Elhami |
| 5,800,558 A | 9/1998 | LaHaise, Sr. |
| 5,800,560 A | 9/1998 | Draenert |
| 5,824,098 A | 10/1998 | Stein |
| 5,824,101 A | 10/1998 | Pappas |
| 5,824,102 A | 10/1998 | Buscayret |
| 5,824,103 A | 10/1998 | Williams |
| 5,824,107 A | 10/1998 | Tschirren |
| 5,824,108 A | 10/1998 | Huebner |
| 5,871,547 A | 2/1999 | Abouaf et al. |
| 5,871,548 A | 2/1999 | Sanders et al. |
| 5,879,387 A | 3/1999 | Jones et al. |
| 5,879,390 A | 3/1999 | Kubein et al. |
| 5,879,392 A | 3/1999 | McMinn |
| 5,879,393 A | 3/1999 | Whiteside et al. |
| 5,879,395 A | 3/1999 | Tornier et al. |
| 5,879,396 A | 3/1999 | Waltson et al. |

| | | | | | | |
|---|---|---|---|---|---|---|
| 5,879,397 A | 3/1999 | Kalberer et al. | | 5,928,288 A | 7/1999 | Wilson |
| 5,879,398 A | 3/1999 | Swarts et al. | | 5,928,289 A | 7/1999 | Deckner |
| 5,879,401 A | 3/1999 | Besemer et al. | | 5,931,870 A | 8/1999 | Cuckler et al. |
| 5,879,402 A | 3/1999 | Lawes et al. | | 5,931,871 A | 8/1999 | Baur et al. |
| 5,879,404 A | 3/1999 | Bateman et al. | | 5,935,171 A | 8/1999 | Schneider et al. |
| 5,879,405 A | 3/1999 | Ries et al. | | 5,935,172 A | 8/1999 | Ochoa et al. |
| 5,879,407 A | 3/1999 | Waggener | | 5,935,173 A | 8/1999 | Roger et al. |
| 5,882,206 A | 3/1999 | Gillio | | 5,935,174 A | 8/1999 | Dye |
| 5,888,204 A | 3/1999 | Ralph et al. | | 5,935,175 A | 8/1999 | Ostiguy, Jr. et al. |
| 5,902,340 A | 5/1999 | White et al. | | 5,938,702 A | 8/1999 | Lopez et al. |
| 5,904,688 A | 5/1999 | Gilbert et al. | | 5,944,756 A | 8/1999 | Fischetti et al. |
| 5,904,720 A | 5/1999 | Farrar et al. | | 5,944,757 A | 8/1999 | Grammont |
| 5,906,210 A | 5/1999 | Herbert | | 5,944,758 A | 8/1999 | Mansat et al. |
| 5,906,643 A | 5/1999 | Walker | | 5,944,759 A | 8/1999 | Link |
| 5,906,644 A | 5/1999 | Powell | | 6,261,289 B1 * | 7/2001 | Levy .................... 606/63 |
| 5,910,171 A | 6/1999 | Kummer et al. | | | | |
| 5,910,172 A | 6/1999 | Penenberg | | | | |
| 5,911,758 A | 6/1999 | Oehy et al. | | | | |
| 5,911,759 A | 6/1999 | Rogala | | | | |
| 5,913,858 A | 6/1999 | Calandruccio et al. | | | | |
| 5,916,268 A | 6/1999 | Schollner et al. | | | | |
| 5,916,269 A | 6/1999 | Serbousek et al. | | | | |
| 5,916,270 A | 6/1999 | Lipman | | | | |
| 5,919,236 A | 7/1999 | Pfaff et al. | | | | |
| 5,928,285 A | 7/1999 | Bigliani et al. | | | | |
| 5,928,286 A | 7/1999 | Ashby et al. | | | | |
| 5,928,287 A | 7/1999 | Keller | | | | |

FOREIGN PATENT DOCUMENTS

| | | |
|---|---|---|
| EP | 0 066 092 | 4/1982 |
| EP | 0 190 446 | 12/1985 |
| EP | 0 253 941 | 7/1986 |
| EP | 0 329 019 | 2/1989 |
| EP | 0 308 081 | 3/1989 |
| GB | 2 069 338 | 8/1981 |
| GB | 2 126 096 | 3/1984 |

* cited by examiner

BONE GROWTH PROMOTING IMPLANT

FIELD OF THE INVENTION

The present invention relates generally to bone implants. More specifically, the present invention relates to bone-growth promoting implants and implants that promote the growth of composite bone material.

BACKGROUND OF THE INVENTION

Conventional bone prostheses or implants that are known in the art generally include a metal portion constructed of steel or titanium inserted in and fixedly attached to a bony portion of a patient's body. For example, conventional implants for stems of articulating joints or for nail-like implants used for intramedullary fixation to support bones during healing of fractures are constructed of metal. The nail-like implants are usually, but not always, removed when healing is complete.

Current implant technology may be divided into two broad categories: implants which require reaming of an inner canal in the bone before insertion of the implant, generally typical of relatively thick implants; and implants which do not require reaming of a bone canal, generally typical of relatively thin implants. Thin implants are easier to insert and they enable better nourishment of the bone and faster healing. However, thin implants provide a less stable support structure for the bone.

Several problems are associated with conventional bone implants due to a mismatch between materials properties of the bone and the metal implant. For example, contact between the metal implant and the bone may cause fretting wear of the bone. Also, a difference in materials properties such as Young's modulus and thermal expansion coefficient between the metal implant and the bone may result in poor anchoring of the metal implant to the bone, which may cause discomfort to the patient, especially during weather changes. Furthermore, conventional metal implants provide virtually no shock absorption or damping.

It is generally known that a bone grows or generates new bone tissue according to the level of stress to which it is subjected within an identified range of stress levels that is less than or equal to a certain maximum stress level but greater than or equal to a certain minimum stress level. One problem with conventional metal implants is that they tend to distribute stress unevenly to the surrounding bone, with some surrounding bone areas receiving excessive stress levels and other surrounding bone areas receiving less than optimal stress levels. In extreme cases where the amount of stress imparted to a surrounding bone area is too low, the conventional metal implant may contribute to atrophy or degeneration of the area because of lack of use. This, in turn, may lead to bone recession and loosening of the anchoring of the metal implant, thus creating an undesirable gap between the bone and the metal implant.

Another problem with conventional metal implants is their tendency to interfere with diagnostic techniques such as magnetic resonance imaging (MRI) and related tomographic techniques. Metal implants produce shadows, or image artifacts, because the metal material of the implants tends to interfere with the magnetic characteristics of the implant region, thus distorting the magnetic image of that region. These shadows reduce the effectiveness of magnetic resonance techniques, which are important and widely used diagnostic techniques that have even been used during surgical operations to produce real-time images with simultaneous multiple image sections. Therefore, the use of non-metal implants would be advantageous because such implants are expected to reduce the presence of these undesirable shadows, or image artifacts, to a level that will preserve the effectiveness of MRI-type images for diagnosis.

Yet another drawback of conventional implants is their inability to conform to the three-dimensionally curved surfaces of a bone canal, thus reducing their effectiveness in inducing or promoting continuous bone growth or bone reinforcement for strengthening the bone.

In order to overcome the aforementioned problems, a number of implants with resilient portions have been proposed in International Application No. PCT/IL96/00098, which was filed Sep. 4, 1996 and invented by the inventor of the present invention, the disclosure of which is incorporated herein by reference. This PCT application discloses various resilient joint prostheses and bone implants that provide shock absorption and promote bone development and growth after implantation. In addition, the PCT application discloses bone implants that are sufficiently flexible that they deform to adapt to various and changing curvatures of the bone.

OBJECTS AND SUMMARY OF THE INVENTION

In view of the above-mentioned considerations, an object of the present invention is to provide an improved bone implant that promotes bone development and growth after implantation, and that improves bone strength through the formation of a composite bone material.

Another object of the present invention is to provide a means for controlling the distribution of stress within a bone and for producing a stress field having an intensity and pattern that acts to prevent bone degeneration and promote growth of new bone tissue to strengthen selected regions of the bone.

Yet another object of the present invention is to provide a means for producing and controlling micro-movement along a substantially continuous surface of a bone that interfaces and interacts with an implant to promote improved generation of new bone tissue from the micro-movement.

The present invention provides implants with new features that are not disclosed in the PCT application PCT/IL96/00098 invented by the inventor of the present invention.

According to the present invention, a high degree of flexibility and control is imparted to a nail-like implant by using a "spar" construction with adjustable tension cables and longitudinal structural members. The tension cables provide curvature control and support, and rigidity against bending and buckling of the nail-like implant. The longitudinal structural members and the tension cables become an integral part of a composite regenerated bone, which has a substantially increased strength over bone regenerated through the use of conventional implants, regardless of whether the nail-like implant remains inside the bone or whether a majority of the implant (except for the longitudinal structural members) is later removed. The flexibility of the implant is controlled by specifically varying the structural geometry and stiffness of certain portions of the implant, and by adjusting the tension in selected tension cables during and/or after the implantation operation to thereby adjust the stiffness of the implant. When the longitudinal structural members are inserted into the bone they have at most a low and generally uniform tension level, and preferably the structural members are free of tension during insertion. After insertion, the tension cables may be adjusted to provide additional stiffness to the longitudinal structural members and to produce a desired curvature therein by imparting asymmetric or non-uniform levels of tension thereto.

The present invention creates a stronger regenerated bone by providing a new type of cross-section for a bone implant and by promoting the growth of a composite bone structure.

DETAILED DESCRIPTION OF PREFERRED EMBODIMENTS

Preferred embodiments of the present invention are described below with reference to the accompanying drawings, in which like reference numerals represent the same or similar elements.

It is generally known that a body recognizes a minimum level of stress in its bones. New bone cells are generated when an amount of stress is exerted thereto that falls within a preferred range of values that are above a certain lower limit and below a certain upper limit. A conventional stem-type or nail-type implant is constructed to have an average geometric shape that does not conform to the three-dimensionally curved surfaces of a bone canal in which the implant is inserted. In addition, contact between the implant and the bone occurs at random regions and is generally not sufficiently continuous to promote optimal bone growth. Because of the randomness of the contact between the implant and the bone, the forces exerted by the implant on the bone produce random stress levels within the bone. Only regions in which the amount of stress exerted on the bone is within a biologically acceptable range are recognized by the body so that new bone cells are generated at those recognized regions. Regions with stress levels below the lower limit or above the upper limit are not recognized by the body resulting in no generation of new bone cells. Thus, the body is prevented from rebuilding its skeletal strength.

The present invention provides a means to control the amount and the distribution of stress imparted by an implant to an adjacent bone, and also provides a means to effect micro-movement at interface regions between the bone and the implant. The implants of the present invention conform to the three-dimensionally curved surfaces of a bone canal such that substantially continuous regions of the bone canal interface with protruding support elements of the implant. The substantially continuous regions include surfaces that contact or interface with support elements with multiple fingers spaced reasonably close to each other, and are positioned to produce a continuous distribution of stress with a desired stress field pattern to promote bone tissue generation and to even tailor bone growth to favor certain bone regions over other regions.

Bone deflection combined with deflection of the implant creates movement in the contact or interface regions, including actual shear movement of the bone relative to the implant, and shear stress in sub-surface regions beneath the contact regions even where there is no actual relative movement. Such micro-movement and micro-change in the stress distribution promotes generation of new bone cells and growth of new bone tissue.

Means for generating and controlling the amount and distribution of stress and for producing micro-movement include:

a) controlling the stiffness of the implant and/or providing means for adjusting the stiffness of the implant, in which reaction of the bone and the implant to bending is adjusted by adjusting tension cables, and in which curvature of the implant is adjusted by adjusting the tension cables; and b) designing protruding support elements that have an appropriate geometry and size and that are made of certain appropriate materials.

Figure 1A:
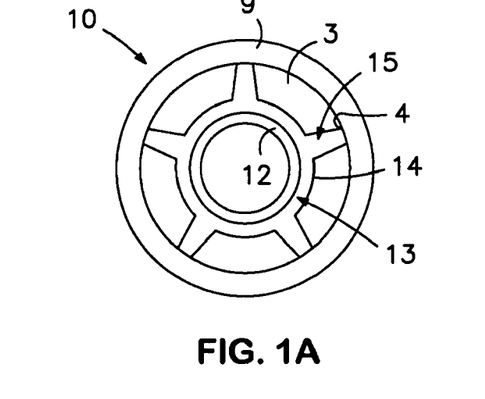
FIG. 1A is a cross-sectional view of a bone implant inserted inside a bone canal according to an embodiment of the present invention.

Turning now to the drawings, FIG. 1A shows a bone implant 10 inserted inside a bone 9, according to an embodiment of the present invention. The implant 10 includes a flexible composite central portion or core 12 embedded or molded inside an interface portion 13. The core 12 may be solid or hollow and is preferably formed of a composite material which may be reinforced with a high-performance material such as DYNEEMA™, which is a fiber made from ultra-high molecular weight polyethylene, for example. The interface portion 13 includes a tubular layer 14 and a plurality of support elements 15 radially protruding outwardly therefrom. The support elements 15 contact the bone 9 by snugly fitting inside a bone canal 4 of the bone 9. Preferably, the support elements 15 occupy only a fraction of the bone canal 4, and zones 3 are located between respective support elements 15 to accommodate natural spongy bone as well as bone marrow. Therefore; the implant 10 permits the spongy bone zones 3 and the bone marrow to internally nourish the bone 9 through the bone canal 4, which is unlike conventional prior art devices that occupy nearly the entire bone canal so that the bone is nourished only from outside of the bone.

Figure 1B:
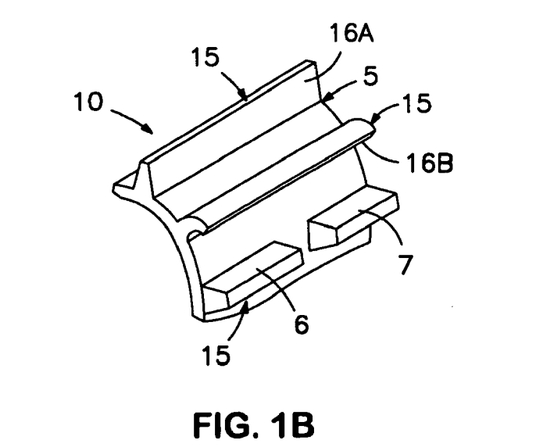
FIG. 1B is a perspective view of a portion of the bone implant of FIG. 1A showing various constructions of support elements according to an embodiment of the present invention.

FIG. 1B is a perspective view of a portion of the bone implant 10. The support elements 15 may extend longitudinally along the entire length of the implant 10, as indicated by reference numeral 5. Alternatively, the support elements 15 may be comprised of two or more longitudinal segments, as indicated by reference numerals 6 and 7. The support elements 15 also may have various shapes. For example, reference numeral 16A shows a standard-type support element having a straight lateral profile and a trapezoidal cross section, and reference numeral 16B shows a spring-type support element having a straight lateral profile and an arcuate or hook-like cross section. According to a preferred embodiment, the support elements 15 deform during insertion of the implant 10 into the bone canal 4 to produce a snug fit that presses against an inner wall of the bone 9 (see FIG. 1A), thereby fostering an excellent and substantially continuous fit of the implant 10 to a patient's specific bone geometry.

The implants 10 may be used in conjunction with a method for adapting an implant to a particular bone by means of a computer-aided bone geometry duplicator, as disclosed in PCT application PCT/IL96/00098, which was invented by the inventor of the present invention. According to this method, the computer-aided duplicator is used inside the operating room to cut the implant 10 to a specific desired shape during an operation.

In a typical implantation operation in which a nail-like implant is inserted into a patient, the patient's bone is drilled to accommodate the implant's particular shape. For implants having stems, such as stems attached to articulating joints, the bone drilling and shaping is done by the surgeon performing the implantation operation. The surgeon uses various files and reamers to prepare the bone for receiving the stem therein. Typically, a number of reamers of various sizes from small to large are used to ream a cavity in the bone and shape the cavity to correspond to the shape of the stem.

According to the present invention, less bone is removed than in the typical implantation operation, and mostly spongy bone material is removed instead of the dense bone material that is reamed out in a conventional implantation operation, which can reduce considerably the strength of the remaining bone. A spoon may be used as a scooping device for removing the spongy bone material to thereby create a cavity in the bone into which an implant of the present invention, with its protruding and flexible support elements, is inserted. The scooping device may contain one or more sensors attached to an elongated flexible core of the scooping device so that when the core is inserted into the cavity the sensors contact and press outwardly against the cavity surface to generate surface geometry data that is fed into a computer. Alternatively, a sensing apparatus separate from the scooping device may be used to generate the surface geometry data for the cavity. The surface geometry of the cavity may also be determined using various diagnostic techniques such as MRI and/or other tomographic techniques.

Once the surface geometry of the cavity is known, a compact computerized shaping tool, adapted for use in an operating room environment, may be used to shape the implant to fit the cavity. For an implant having support elements 16A (see FIG. 1B), the implant may be formed by first using the shaping tool to produce the implant without the support elements 16A, and then individually machining each of the support elements 16A one at a time, similar to duplicating a key, to produce a substantially close three-dimensional fit of the implant in the cavity.

Figure 1C:
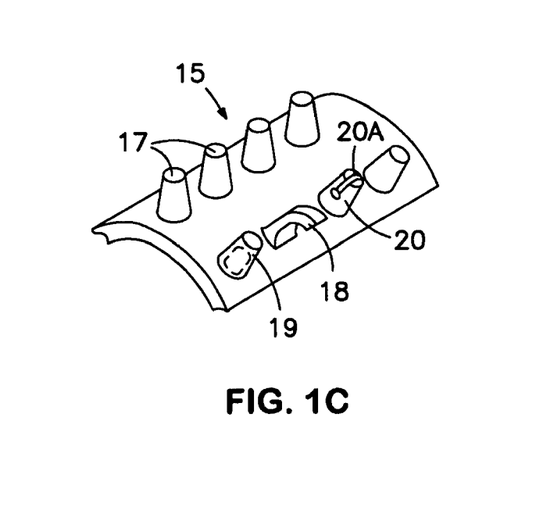
FIG. 1C is a perspective view of a portion of the bone implant of FIG. 1A showing an alternative construction of support elements according to an embodiment of the present invention.

FIG. 1C illustrates an alternative construction of the support elements 15, according to an embodiment of the present invention. The support elements 15 may include tapered stub-type protrusions 17, substantially deformable and springy hook-type protrusions 18, or tapered stub-type hollow protrusions 19. The hook-type and hollow protrusions 18, 19 deform during insertion into the bone canal 4 and press against an inner wall of the bone 9 (see FIG. 1A), thereby providing an excellent fit to the patient's specific bone geometry. According to a preferred embodiment, the tapered stub-type protrusions 17 have a slender profile, allowing them to deflect during insertion of the implant 10.

The support elements 15 may also be comprised of other protrusions of various desired shapes. For example, reference numeral 20 shows a support element consisting of a tapered stub-type protrusion with at least one channeled groove 20A formed therein for receiving a tension cable (not shown), which is described hereinbelow. (The term "cable" represents any longitudinal member with an arbitrary cross section, and may be formed of materials such as woven elements, rods, bars, and the like.) Some of the protrusions may be cut using a computer-aided bone geometry duplicator to produce a nearly exact customized fit.

Figure 2A:
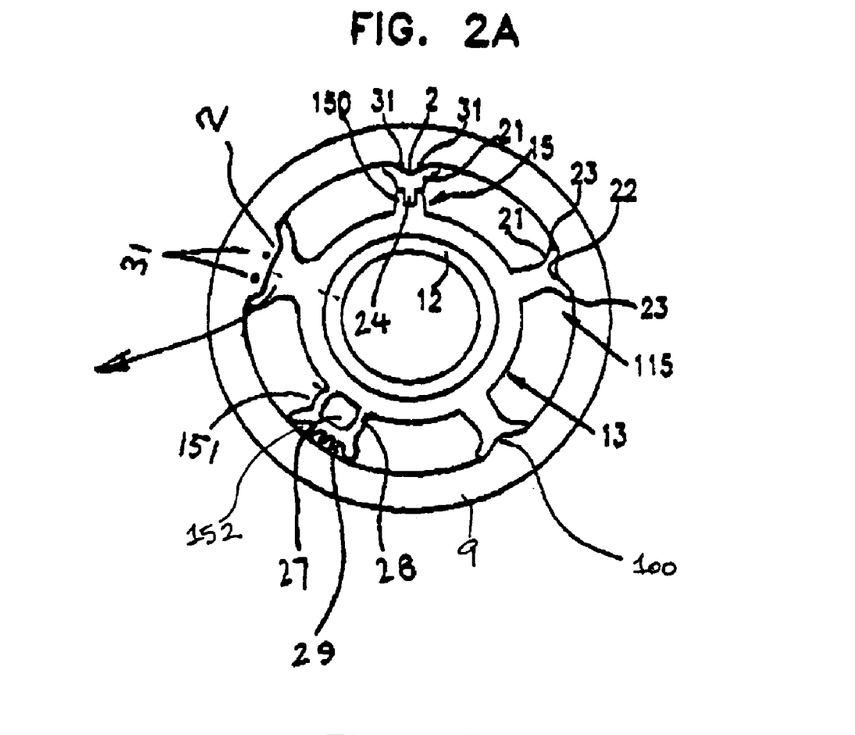
FIG. 2A is a cross-sectional view of a bone implant having support elements according to another embodiment of the present invention.

FIG. 2A is a cross-sectional view showing various types of support elements 115, according to another embodiment of the present invention. Each of the support elements 115 include a trough portion 21, a floor 22, and side walls 23. As indicated by reference numeral 150, the support elements 115 may be made of two separate portions, such as a trough portion 21 having a male connecting member 24 forming a first portion that mates with a female slot member 25 formed between a pair of raised or serrated walls 26 extending from the interface portion 13 forming a second portion, for example.

Figure 2B:
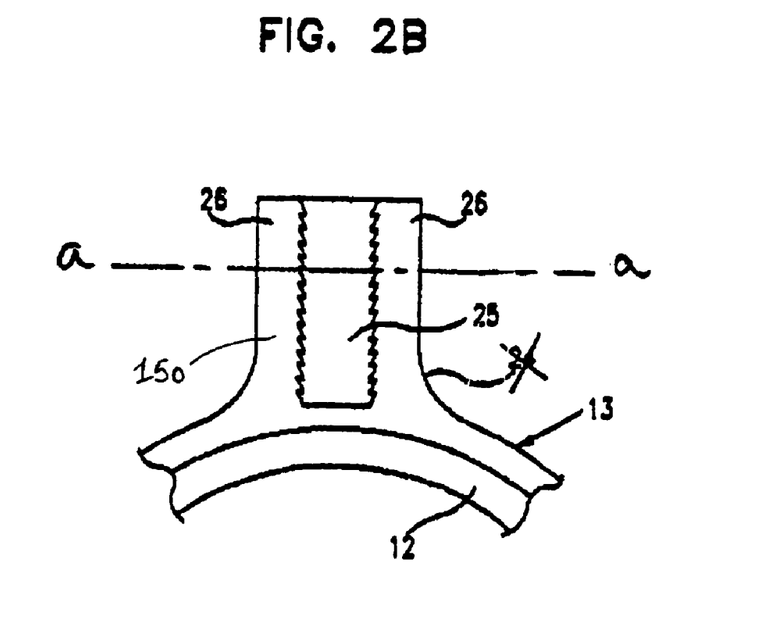
FIG. 2B is a cross-sectional view of a support element of FIG. 2A.
Figure 2C:
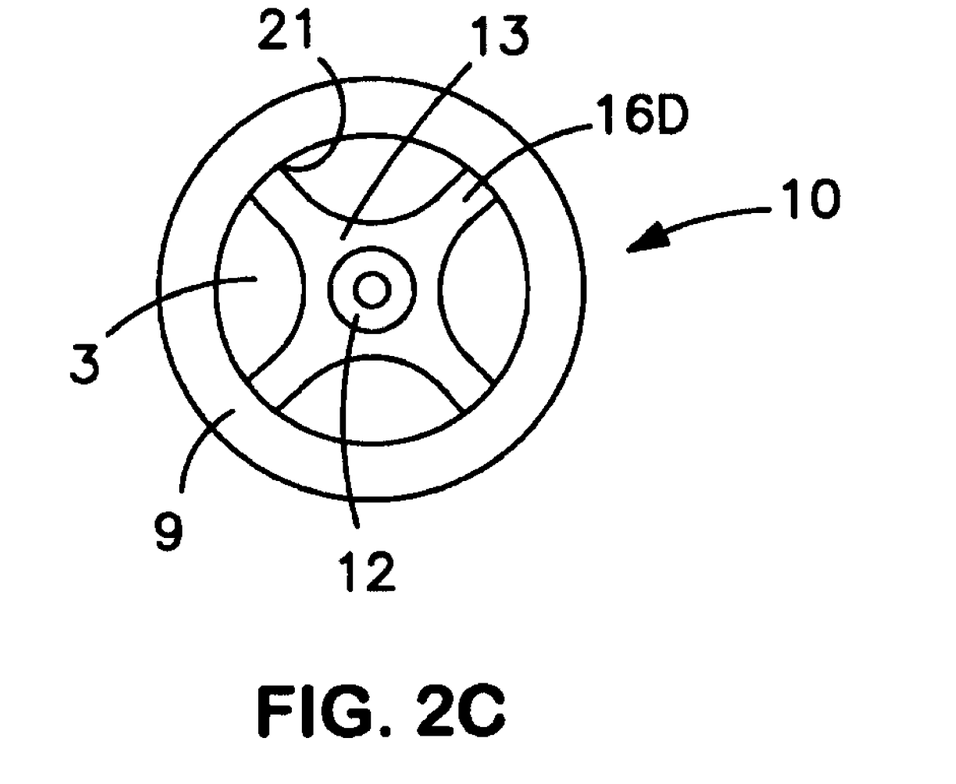
FIG. 2C is a cross-sectional view of a bone implant inserted inside a bone canal according to another embodiment of the present invention.

FIG. 2C is a cross-sectional view showing a bone implant 10 inserted inside a bone 9 according to another embodiment of the present invention. The implant 10 includes a trough portion 21 constructed as an integral part of the interface portion 13. Protruding portions 160 serve as support elements 115 for the implant 10. Zones 3 are located between respective protruding portions 160 to accommodate natural spongy bone as well as bone marrow, thereby permitting the bone 9 to be nourished internally from within the bone 9. The zones 3 may also be used as a mold for the growth of new bone tissue.

A computer-aided bone geometry duplicator may be used to cut the raised walls 26, for example along an orientation line indicated by a-a, as shown in FIG. 2B, so that the trough portion 21 is tailored to snugly press against the inner wall of the bone 9. The computer-aided duplication device takes into account the dimensions of the trough portion 21, which preferably is of a uniform section. A number of different connections between the trough portion 21 and the interface portion 13 are possible, including a smooth fit, a spring fit, a click-on fit, or a serrated fit. The computer-aided bone geometry duplicator may also be used to custom-cut the protruding portions 160 of the bone implant 10 of FIG. 2C.

As indicated by reference numeral 151 in FIG. 2A, the support elements 115 also may be formed of at least one integral portions connected to the trough portion 21 and having a spring-type connecting member (not shown) or a hollow-type connecting member 28 with a void 27 therein. Both types of connecting members deform during insertion of the implant 10 into the bone canal 4 to snugly fit and press against the inner wall of the bone 9 (see FIG. 2A), thereby fostering an excellent and substantially continuous fit to the patient's specific bone geometry. In addition, the trough portion 21 may be provided with fingers 29 protruding therefrom to engage the inner wall of the bone 9 to exert pressure and generate micro-movement, thus serving as a catalyst to promote the generation of new bone tissue growth into a space 152 contained by the trough portion 21.

Figures 3A, 3B:
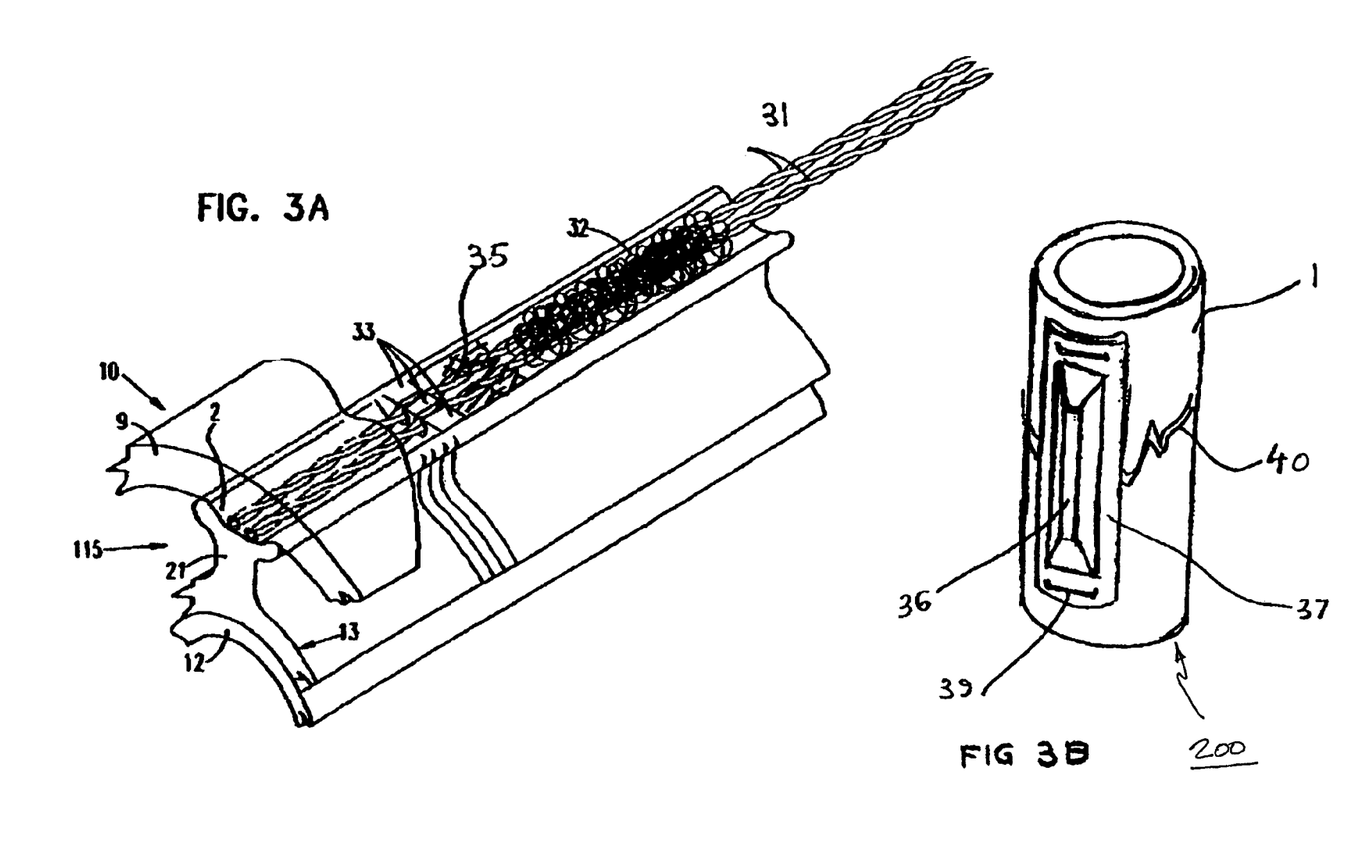
FIG. 3A is a perspective view of a support element of FIG. 2A.
FIG. 3B is a perspective view of a brace element externally attached to a fractured bone.

FIG. 3A is a longitudinal perspective view of one of the support elements 115 of FIG. 2A. The trough portion 21 may be fitted with an adjustable longitudinal support structure or tension cables 31 made of high-performance materials such as steel, DYNEEMA™, carbon, or aramid fibers such as KEVLAR™, for example. The tension cables 31 may include metal fibers, which serve as x-ray markers for indicating the presence of the implant in an x-ray film. The tension cables 31 are supported by bridge elements 33.

The tension cables 31 may be uncoated or they may be coated or surface-treated with special materials such as hydroxyapatite, such as porous (PHA) and non-porous (NPHA) versions of granular hydroxyapatite, for stimulating bone calcification; porous bone material; inorganic bovine bone; inorganic zenograft bone mineral; an osteoconductive bone graft substitute (a type of corraline hydroxyapatite), such as that marketed under the name PRO OSTEON™; a bioactive glass implant that bonds to bone and tissue at a fracture site, such as that marketed under the name BIO-GLASS™; and COLLAGRAFT™, an FDA-approved osteoconductive and osteoinductive synthetic bone graft substitute that contains a mixture of hydroxyapatite, tricalcium phosphate, and bovine fibrillar collagen, among other things. The coating may contain bone morphogenic protein and/or prescribed medication for preventing bone diseases.

The tension cables 31 may be wrapped with a randomly woven loose mesh of thin fibers 32, and may also include short whisker reinforcement elements 35 made of the same or similar materials as the tension cables 31. The mesh 32 and the whisker reinforcement elements 35 may be coated with special materials such as hydroxyapatite, with or without bone morphogenic protein and/or prescribed medication for preventing bone diseases, and the whisker reinforcement elements 35 may be included as part of the mesh 32. Preferably, the mesh 32 and the bridge elements 33 are formed of a resorbable material that is absorbed by the patient's body so that they practically disappear within a prescribed period of time.

The presence of such materials as hydroxyapatite, with or without bone morphogenic protein, on the trough portion 21, the mesh 32, and/or the tension cables 31 promotes new bone tissue generation, and the new bone tissue may be specially designed to have a predetermined shape defined by the shape of the trough portion 21, which serves as a mold for the new bone tissue generation. Over time (about one year in some cases), a composite bone is produced with a cross section having a larger moment of inertia than the original moment of inertia of the bone 9, and the composite bone is formed as a substantially continuous longitudinal web 2 that interfaces with the trough portion 21, with or without the high-performance tension cables 31 being embedded therein. The tension cables 31 may be fully or partially embedded within the new bone tissue, and the tension cables may be bonded to the bone 9 by the new bone tissue and/or by an adhesive substance.

Therefore, the implant 10 not only effectively helps to heal a broken bone, it also substantially increases the strength of the healed bone by effectively reforming the bone with a new cross section having a larger moment of inertia (I) than that of the original bone's internal structure, and by incorporating reinforcements, such as the tension cables 31, which may or may not be used to provide adjustable tension control, formed of a material with a Young's modulus (E) greater than that of natural bone. The overall product of E×I of the composite bone is thus much higher than that of the original or natural bone. Therefore, the danger that the same bone will break again is reduced. The newly-induced bone tissue growth may also incorporate and have embedded therein the whisker reinforcement elements 35, which act to further strengthen the newly-generated bone material.

According to another embodiment of the present invention, bone-growth inducing materials and/or prescribed medications for preventing bone diseases may be included as a coating on the implant 10 or administered by various means as crystals, resorbable capsules, liquids, or powders into open regions or voids in the implant 10.

According to an embodiment of the present invention, whisker reinforcement elements, similar to those of reference numeral 35, made of metal or fibers of carbon, KEVLAR™, or DYNEEMA™, for example, are added to bone cement for improving the strength of a cement layer formed of the whisker-reinforced cement to reduce the occurrence of cracking in brittle types of cement and to improve stability in flexible types of cement. The reinforced bone cement may be used in attaching various bone implants to bone, and may also be used to connect bone segments together.

FIG. 3B shows an embodiment of the present invention for a stand-alone external bone brace 200, which operates as a bone-structure enhancement device that may also be used to facilitate the generation of composite bone. The bone brace 200 comprises a trough portion 36 formed as a corrugated portion of a thin bone brace 200 integrally attached to a sleeve-flange element 37. Alternatively, the bone brace 200, may be comprised of a trough portion 36 formed as a molded recess (not shown) of a thick bone brace 200. The bone brace 200 may be secured by cement, glue, staples 39, screws, or other means onto the outside of a fractured bone 1, around either the entire circumference of the bone 1 or a part of it, to locally reinforce the bone 1 at specific regions such as at the fractured region 40 to repair the fractured region 40. Optionally, the sleeve-flange element 37 with the attached trough portion 36 may be secured to a region to change the bone curvature of that region.

The trough portion 36 is, in many respects, similar to the trough portion 21 of FIG. 3A, and may be fitted with tension cables 31 such as those described above. The tension cables 31 may or may not be adjustable.

In some cases, preferably in cases where the sleeve-flange element 37 encircles the bone 1, a woven reinforcement bandage (not shown) formed of high-performance materials (such as those described above) may be placed between the surface of bone 1 and the sleeve-flange element 37. The reinforcement bandage has incorporated therein growth-inducing biological materials to promote bone tissue growth through and around the weave of the bandage, thus promoting the growth of a new bone layer to which the reinforcement bandage is bonded. The woven reinforcement bandage may be constructed as an integral layer of the sleeve-flange element 37 such that some of the fibers of the woven bandage are laminated and bonded into a skin layer of the sleeve-flange element 37.

According to an embodiment of the present invention, the woven reinforcement bandage is fully embedded within the newly generated bone layer. That is, when new bone regeneration occurs, the sleeve-flange element 37 becomes embedded or "cast" into the new bone material and becomes a single structural element with the new bone material.

Figure 4A:
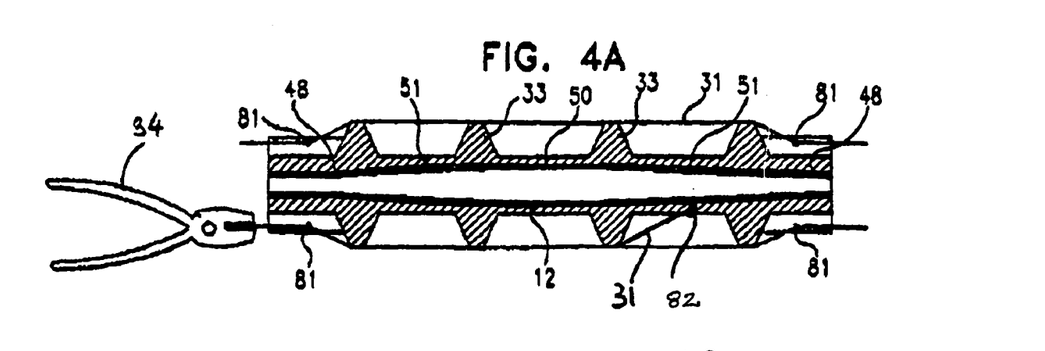
FIG. 4A is a longitudinal cross-sectional view of a bone implant according to one embodiment of the present invention.

FIG. 4A is a cross-sectional view of the bone implant 10 showing the core 12 (see FIGS. 1A and 3A). The core 12 has a stiffness governed by, among other things, its overall geometry and materials properties. The core 12, the bridge elements 33, and the generally-taut tension cables 31 combine to form a "sailboat's spar" configuration, which is very light and has a much higher combined stiffness than that of the core 12 alone. The bridge elements 33 serve as "spar spreaders" and may be constructed as a portion of the support element or as a portion of the core 12. Optionally, the composite core configuration may be employed without the spar configuration, and the spar configuration may be employed at only a portion of the implant 10.

The core 12 may be formed of any material, and may have various constructions, such as a solid unit, a hollow unit, an assembly of individual rods, a plurality of rods formed into a truss structure, a mesh of circumferential fibers or wires wound to have a substantial area of open voids, or helical (coiled) springs.

The tension cables 31 may be anchored at any location of the implant 10, such as at anchoring points 81, 82, or other alternative locations, and the tension in the tension cables 31 may be controlled and adjusted during the course of the implantation operation at any time during and after insertion of the implant. Therefore, the tension in the tension cables 31 may be adjusted after the implant is inserted into and positioned within the bone canal 4, and may even be further adjusted at future times after the implantation operation.

The tension cables 31 are adjusted using a tensioning device 34, which may include a multi-pin ratchet means or other means that enable the tensioning device 34 to change or adjust the tension in the tension cables 31 and also to cut extraneous lengths of the tension cables 31 after tensioning thereof. The tension cables 31 may be adjusted to provide stiffness to at least a portion of the implant 10, and they may also be used to produce a curved profile in at least a portion of the implant 10 so that the curved portion has a substantially identical profile as that of the bone canal 4, even while outside of the bone canal 4. The above-described tension system is an "even tension" type of tension system.

According to an embodiment of the present invention, the tensioning device 34 may be used to produce a controlled and uneven tension in the tension cables 31 to simulate a bending moment in the bone. Implants 10 having tension cables 31 with an uneven or non-uniform tension thereof may be used as a loaded element that continuously acts on the bone to change its curvature over time. Therefore, such tension cables 31 may be used to correct undesired curvature in bones, and the correction process may include periodic adjustments of the tension in the tension cables 31 to progressively correct the undesired bone curvature.

As an alternative, whisker reinforcement elements 35 may be included in some trough portions 21 of the implant 10 and not in others to produce controlled stress regimes which may be used to exert controlled levels of stress to selected areas of the bone 9 to thereby achieve bone curvature correction. The presence of whisker reinforcement elements 35 in newly generated bone tissue changes the characteristics of the bone as compared with natural bone tissue without the presence of the whisker reinforcement elements 35.

Figure 5:
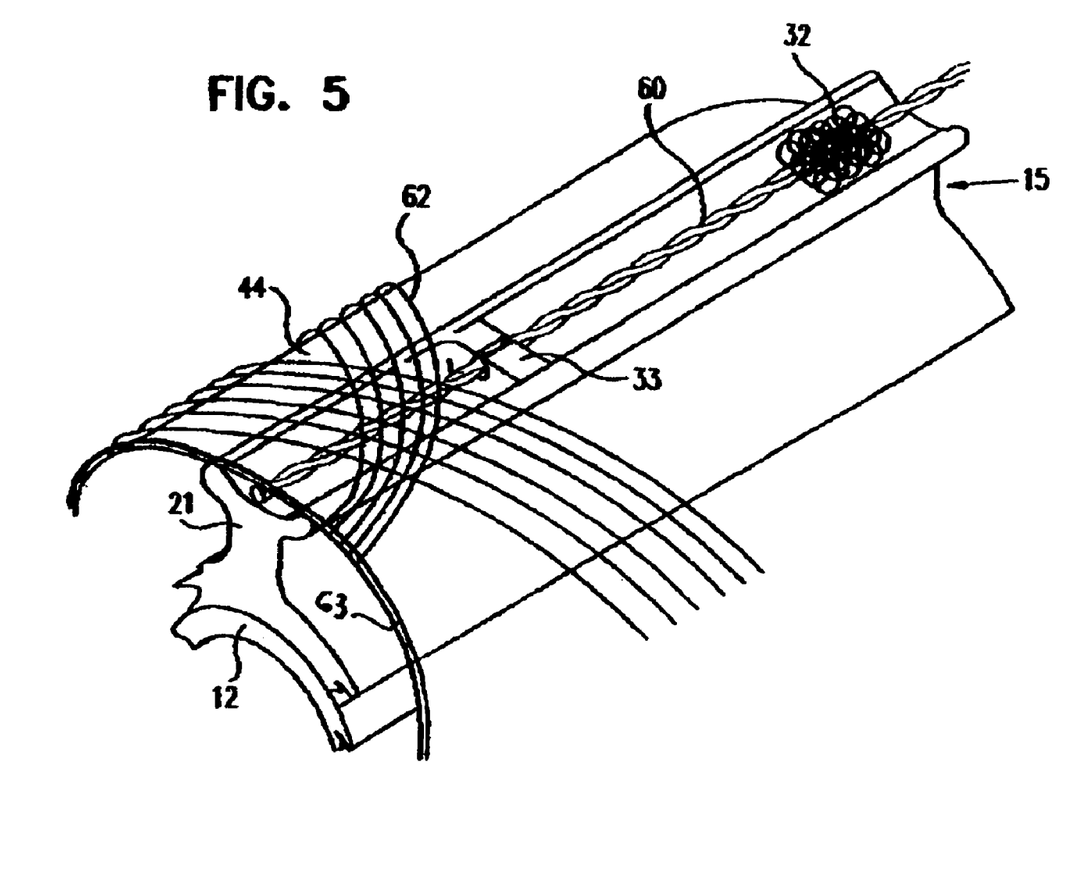
FIG. 5 is a perspective view of a tension cable and a woven sleeve element according to an embodiment of the present invention.

According to another embodiment of the present invention, the implant 10 may be constructed to include tension cables 31 but not include trough portions 21 by using various "spreaders means" such as the support elements 15, shown in FIG. 1C, at least for the purpose of controlling stiffness and curvature, or as a longitudinal cable 60 integrally woven into a sleeve element 62, as shown in FIG. 5.

Figure 4B:
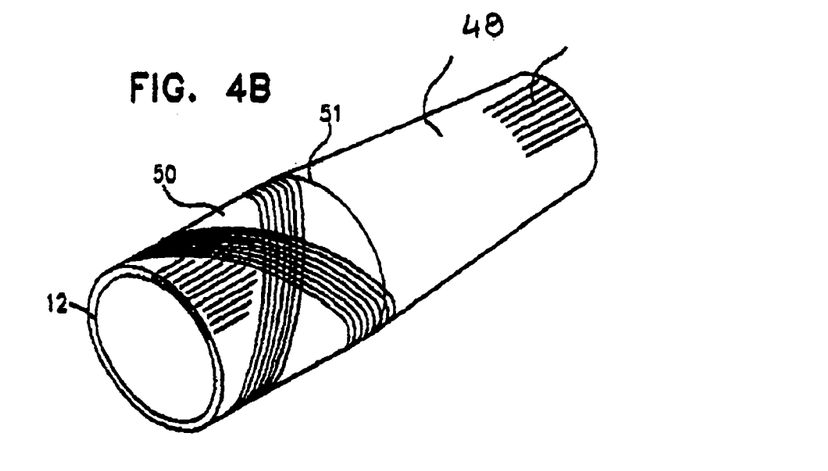
FIG. 4B is a perspective view of an embodiment of a core of the bone implant having one or more tapered ends according to the present invention.

FIG. 4B shows an embodiment of the core 12 formed of a composite material and constructed to have one or more tapered ends 48. Positioned between a pair of knuckles 51 is a middle section 50 having either a constant or varying cross-sectional diameter. The composite material may include a number of different fiber types, orientations, and diameters to optimize the desired stiffness for different portions of the core 12. The middle section 50 is designed to be the stiffest part of the core 12 so that it may provide stability to bone regions that most require stiffness, such as near an articulating joint portions or at a fractured bone region, while the tapered ends 48 are sufficiently flexible to enable easy insertion of the implant 10 into the bone's three-dimensionally curved canal and, at the same time, provide good anchoring to the bone. The tapered ends 48 become stiffer after insertion into the bone through a tensioning action of the tensioning cables 31, as described above.

According to a preferred embodiment, the core 12 is formed of at least two types of materials each having a different Young's modulus, and the at least two types of materials are arranged to provide a varying Young's modulus along a longitudinal axis of the core 12.

Figure 4C:
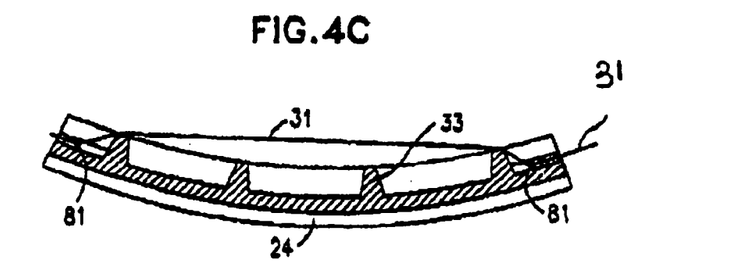
FIG. 4C is a longitudinal cross-sectional view of tension cables anchored to a support element of the bone implant according to an embodiment of the present invention.

FIG. 4C is a longitudinal cross-sectional view showing a tension cable 31 anchored to a trough portion 21. The trough portion 21 may have a natural slightly curved profile such that the tension cable 31 is supported on only a part of end bridge elements 33. When fitted into the slots 25 in the molded interface portion 13 (shown in FIG. 2B), the trough portion 21 straightens and is kept straight by the raised or serrated walls 26 that produce a secure fit, as described above with respect to FIGS. 2A and 2B, or by holding means which may be of a ring type (not shown) that prevents the trough portion 21 from reverting to its original curved shape. This creates a pre-designed tension in the tension cable 31, and the tension is similar to that in strings on a musical instrument or stays on a sailboat spar fitted with spreaders. This insertion tension may be the final tension of the assembled implant or, alternatively, the insertion tension may be an auxiliary tension, with a higher final tension exerted by the action of the tensioning device 34. Adjustments to the tension in one or more tension cables 31 may be made during the course of the implantation operation or after insertion of the implant, such that final tension adjustments are made only after the device has been inserted into and positioned within the bone canal 4, as mentioned above.

The implant 10 and the treated bone 9 may thus form two structure types: one in which the implant 10 is transformed into the bone 9, and one in which the implant 10 is superimposed with the bone 9.

According to the first structure type, an assembly of three components—a composite core 12, bridge elements 33, and tension cables 31—is transformed into a structure that comprises natural bone, bone tissue generated as bone webs 2, and tension cables 31. These components become incorporated in a composite bone structure when new bone web tissue is generated that fills the trough portion 21 and embeds the tension cables 31 within the newly generated bone web tissue, thereby reinforcing the web tissue. Other portions of the implant 10, excluding the tension cables 31 may be removed from the patient.

According to the second structure type, an assembly of the three components—a composite core 12; bridge elements 33; and tension cables 31—is superimposed with a structure that comprises natural bone, bone tissue generated as bone webs 2, and tension cables 31. These components become incorporated in a composite bone structure when new bone web tissue is generated that fills the trough portion 21 and embeds the tension cables 31 within the newly generated bone web tissue, thereby reinforcing the web tissue.

FIG. 5 is a perspective view showing a longitudinal cable 60 and support element 15 according to another embodiment of the present invention. The longitudinal cable 60 may be part of a woven sleeve element 62 made of high-performance fibers of DYNEEMA™, carbon, or KEVLAR™, for example. Groups of fibers are woven into various layers and have various orientations such as diagonal, longitudinal, and circumferential, for example, and may also have open areas 44 in the weave. The sleeve element 62 may be attached to the support element 15 or to the trough portion 21 by various click-on means (not shown), by using one or more bridge elements 33, or by using one or more channeled grooves 20A (see FIG. 1C).

The sleeve fibers may contain special materials such as hydroxyapatite, with or without bone morphogenic protein. Additionally or alternatively, the sleeve element 62 may include regions containing a loose mesh 32 of thin fibers made of the same or similar materials as the sleeve element 62, and may also contain special materials such as hydroxyapatite, with or without bone morphogenic protein, or a prescribed medication, such as that for fighting bone or bone marrow diseases. Optionally, the sleeve element 62 may be wrapped with the loose mesh 32.

The implant 10 is inserted into the sleeve element 62 and the sleeved implant is then inserted into the bone canal 4, with the sleeved implant snugly contacting the bone 9 at a plurality of generally continuous locations. Optionally, a lining 63 may be interposed between the implant 10 and the sleeve element 62, and may be constructed to flexibly assist in pressing the sleeve element 62 against the bone canal 4 to promote a substantially continuous contact between the implant 10 and the bone canal 4. At the contact regions, the presence of growth-inducing biological materials helps to promote bone tissue growth through and around the weave, thus creating a new bone layer to which the sleeve element 62 becomes bonded. In one embodiment, the sleeve element 62 becomes fully embedded within the new bone layer, thus creating the composite bone described above. The openings 44 are designed to encourage spearheads of bone growth to penetrate the weave quickly, and then gradually spread laterally until a generally uniform layer of new bone tissue is generated. The mesh 32, the whisker reinforcement elements 35, and/or the tension cable 60 act to promote bone tissue generation to conform to a predetermined desired shape defined by the trough portion 21, which also serves as a form or mold for embedding the tension cable 60 in the newly generated bone tissue.

Thus, bone growth into the trough portion 21 and/or the sleeve element 62 may occur in a number of ways:

(a) by natural bone regeneration with time;

(b) by application of pressure using various implant portions;

(c) by micro-movement and/or vibration of portions of the implant relative to the bone canal;

(d) by micro-movement and/or vibration of fixed or resorbable whisker reinforcement elements relative to bone canal; and (e) by administering various bone-growth promoting materials.

The composite bone and the structurally improved implants of the present invention may be employed in cases where no bone fracture is present but where bone reinforcement is necessary and desired. The implant 10 may be used as a "non-structural device" made of a relatively thin skin of a material such as polyethylene, for example, which is easily inserted into the sleeve element 62 and which may include the tension cables 31, the mesh 32, and/or the whisker reinforcement elements 35. Such a device is inflated by fluid pressure to press against the wall of the bone canal 4.

According to yet another embodiment of the present invention, at least one region of the interface portion 13 may be inflatable and filled with fluid to create pressure regions which, in turn, exert forces on the support members 15 and the wall of the bone canal 4 to effect anchoring of the implant 10 and/or to produce a snug fit of the implant 10 within the bone canal 4 to thereby enhance the micromovement of the implant 10 relative to the bone canal 4.

According to still another embodiment of the present invention, and with reference to FIG. 1A, a flexible implant is constructed without a core element 12, thus making the implant extremely flexible and easy to insert into the bone canal 4. The interface portion 13 of the flexible implant may be reinforced by high-pressure tubing made of fibers of materials such as steel, nylon, polyester, KEVLAR™, and DYNEEMA™, for example. By filling the area surrounded by the interface portion 13 with fluid, which exerts pressure on the interface portion, the flexible implant is transformed from an extremely flexible state to a substantially rigid state. The pressure exerted by the fluid on the interface portion 13 also acts to press the support elements 15 against the wall of the bone canal 4, thereby producing an optimal fit and good anchoring of the flexible implant in the bone canal 4.

For an implant such as that shown in FIG. 5, the pressure exerted by the fluid on the interface portion 13 presses the sleeve element 62 against the wall of the bone canal 4 to produce a nearly continuous contact between the sleeve element 62 and the wall of the bone canal 4 over a substantial portion of the sleeve element 62. Optionally, if a lining 63 is used in the flexible implant, the interface portion 13 presses the lining 62 which, in turn, presses the sleeve element 62 against the wall of the bone canal 4.

Once the interface portion 13 is pressurized with fluid, the tension cables 31 may be adjusted to produce desired tension levels in various parts of the flexible implant.

The flexible implant described above may be provided with short sections of a core element 12 at specific portions of the flexible implant to provide support to those portions.

Optionally, the flexible implant may contain time-release capsules (not shown) that emit controlled amounts of medication into the bone canal 4 over an extended period of time. The time-release capsules may be positioned wherever there is sufficient space available in the flexible implant.

Figures 6A, 6B:
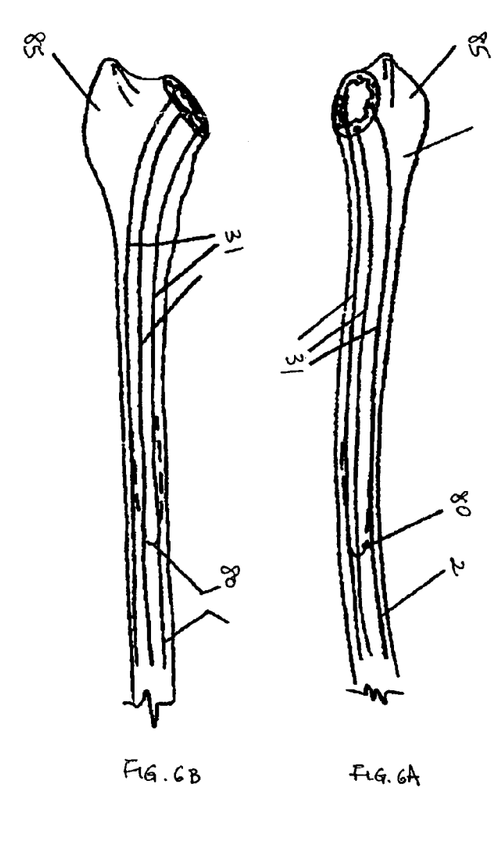
FIGS. 6A and 6B are cut-away views showing tension cables embedded in a web according to an embodiment of the present invention.

FIGS. 6A and 6B are cut-away views showing an embodiment of the present invention as applied to a stem implant such as a hip replacement stem implant. The hip replacement stem implant produces a continuous longitudinal webs 2 reinforced with tension cables 31 embedded therein, and these webs 2 extend beyond the end point 80 of a conventional stem implant. Therefore, overall bone strength is reinforced along the entire femur 85, and the stem implant forms a gradual transition from implant to composite bone to bone.

According to yet another embodiment of the present invention, improvements are made to conventional interlocking nail systems.

In a conventional interlocking nail system a metal nail is used, and the nail has through-holes pre-drilled therein. During the implantation operation the surgeon drills through the bone and must take care to align the bone holes with the pre-drilled holes in the nail. The pre-drilled metal nails are usually coated with a bio-compatible material and, therefore, it is desirable to preserve the integrity of that coating. Screws are then inserted through the holes in the metal nail and are self-tapping with the holes in the bone. This interlocking process prevents axial movement of the bone relative to the nail and ensures that two fractured bone portions are joined and prevented from separating and forming an undesirable space therebetween.

The present invention improves on the conventional interlocking nail system by not requiring the surgeon to align the holes drilled in the bone with the pre-drilled holes in the metal nail, which is a very difficult task to perform during the surgical operation and often results in poorly fitted implants. Instead, according to an embodiment of the present invention, the nail is made of a drillable material so that the surgeon can drill directly through the bone and the nail without having to worry about whether the bone holes align with the nail holes. In addition, the drilling can be accomplished at any desired angle and orientation and is not limited by the presence of pre-drilled holes in the nail.

Figure 7:
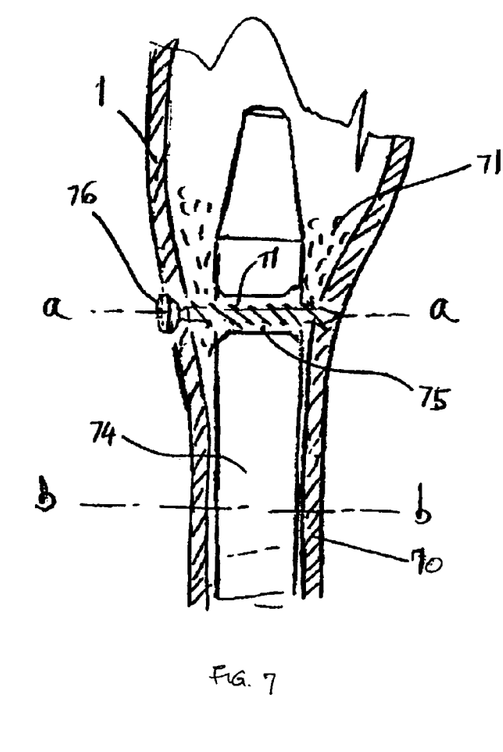
FIG. 7 is a cut-away view showing an improved interlocking nail system according to an embodiment of the present invention.

According to another embodiment of the present invention, shown in FIG. 7, a plastic sleeve 75 is inserted into a pre-drilled hole in a metal nail 74. During the implantation operation, the surgeon drills through the bone 70 and then through the plastic sleeve 75. The plastic sleeve 75 may initially contain a small hole or an elongated slot (not shown) or no hole at all. The plastic sleeve 75 acts to grip the screw 76 to prevent it from sliding in the direction a-a inside the pre-drilled hole in the metal nail 74. The diameter of the pre-drilled holes in the metal nail 74 is necessarily larger than the outer diameter of the threads 77 of the screw 76 because otherwise the screw 76 cannot be inserted therein. The drilled hole in the plastic sleeve 75, however, may be smaller than the outer diameter of the threads 77 of the screw 76 so that the threads 77 of the screw 76 cut into the plastic material of the sleeve 75. According to a preferred embodiment, the sleeve 75 is made of an FDA-approved polyethylene.

The embodiments described above are illustrative examples of the present invention and it should not be construed that the present invention is limited to these particular embodiments. Various changes and modifications may be effected by one skilled in the art without departing from the spirit or scope of the invention as defined in the appended claims.

What is claimed is:

1. A deformable bone implant, comprising a surface defining a bone engaging, resiliently deformable interface portion supported by a resiliently deformable support core and comprising a plurality of resiliently deformable support elements attached to a plurality of adjustable cables in a manner permitting adjustment of the stiffness and/or curvature of the implant.

2. A deformable bone implant according to claim 1, wherein each cable is tensioned to a different degree than the other.

3. A deformable bone implant according to claim 1, and operatively configured to be adjustable before, during, and after implantation of the bone implant.

4. A deformable bone implant according to claim 1, wherein the tension in the adjustable cables is adjusted to provide for a variable rigidity to the bone implant.

5. A deformable bone implant according to claim 1, wherein the implant surface comprises bone engaging protrusions.

6. A deformable bone implant according to claim 1, wherein the implant surface comprises a coating comprising a growth promoting agent.

7. A deformable bone implant for insertion into a bone canal comprising
a surface defining a bone engaging interface portion supported by a support core;
a plurality of resiliently deformable support elements oriented in longitudinal rows along the interface portion and protruding from the interface portion;
wherein the plurality of deformable support elements are structurally configured to allow for a press fit between said implant and the bone canal such that the implant conforms to and fits snugly within the bone canal;
wherein the plurality of resiliently deformable support elements comprise protrusions that are operatively configured to deflect during insertion of the implant into the bone canal and to exert force against said bone canal after deflection when said implant is affixed in said bone canal; and
wherein an adjustable cable is operatively associated with said resiliently deformable support elements in a manner permitting adjustment of tension in the resiliently deformable support elements to thereby adjust stiffness and/or curvature of the implant.

8. A deformable bone implant according to claim 7, wherein the adjustable cable is supported above the surface of at least one of said resiliently deformable support elements.

9. A deformable bone implant according to claim 7, further comprising a plurality of adjustable cables operatively associated with said resiliently deformable support elements in a manner permitting adjustment of tension in the resiliently deformable support elements to thereby adjust stiffness and/or curvature of the implant.

10. A deformable bone implant according to claim 9, wherein the adjustable cables are tensioned to a different degree from one another.

11. A deformable bone implant according to claim 9, wherein the adjustable cables are operatively configured with respect to the resiliently deformable structural elements to allow tension in the cables to be adjusted before, during, and/or after implantation of the bone implant.

12. A deformable bone implant according to claim 9, wherein the implant has different degrees of rigidity along the implant.

13. A bone implant according to claim 7, wherein said implant is coated at least in part about said surface of the implant with a bone growth promoting agent.

* * * * *